United States Patent [19]

Elliott et al.

[11] 3,975,465

[45] Aug. 17, 1976

[54] HETEROCYCLIC PHOSPHORUS COMPOUNDS

[75] Inventors: John Scotchford Elliott, Beaconsfield; Bryan Terence Davis, Wakingham; Monty Frederick Crook, Binfield, all of England

[73] Assignee: Edwin Cooper & Company Limited, Bracknell, England

[22] Filed: Mar. 17, 1975

[21] Appl. No.: 558,809

Related U.S. Application Data

[62] Division of Ser. No. 332,125, Feb. 13, 1973, Pat. No. 3,891,726.

[30] Foreign Application Priority Data

Feb. 18, 1972 United Kingdom............... 7582/72

[52] U.S. Cl.............................. 260/927 R; 260/403; 260/920; 260/936; 260/971; 260/973; 260/978
[51] Int. Cl.²........................................... C07F 9/32
[58] Field of Search............... 260/403, 920, 927 R, 260/936, 971, 973, 978

[56] References Cited
UNITED STATES PATENTS

| | | |
|---|---|---|
| 2,974,158 | 3/1961 | Lanham.......................... 260/927 R |
| 3,092,650 | 6/1963 | McBride et al................. 260/978 X |
| 3,729,532 | 4/1973 | Jungermann et al. ............. 260/936 |

*Primary Examiner*—Richard L. Raymond
*Attorney, Agent, or Firm*—Donald L. Johnson; Robert A. Linn; Joseph D. Odenweller

[57] ABSTRACT

A heterocyclic phosphorus mono-, di- or polyester has the constitution of the product prepared by reacting an intermediate of specified type with a di- or polyol or derivative thereof capable of yielding the di- or polyol on hydrolysis, said intermediate of specified type being a heterocyclic phosphorus compound having the constitution of the compound prepared by reacting an olefin polymer or copolymer having at least 50 carbon atoms and containing olefinic unsaturation with a phosphorus trihalide in the presence of a Friedel-Crafts catalyst, preferably consisting of an aluminium halide, to form a reaction product having halogen atoms attached to phosphorus, and thereafter reacting the reaction product with a hydroxy compound, preferably water or methanol, to remove one or both of the halogen atoms attached to the phosphorus atom. Lubricating compositions containing the mono-, di- or polyesters of the invention are also described.

11 Claims, No Drawings

HETEROCYCLIC PHOSPHORUS COMPOUNDS

This application is a divisional of copending application Ser. No. 332,125 filed Feb. 13, 1973 now U.S. Patent No. 3,891,726.

The present invention relates to heterocyclic phosphorus mono-, di- or polyesters which are particularly useful as lubricating oil additives.

In our copending U.S. application Ser. No. 2,63,450 filed 16th June 1972, now abandoned, there is described an intermediate which is described as a heterocyclic phosphorus compound having the constitution of the compound prepared by reacting an olefin polymer or copolymer having at least 50 carbon atoms and containing olefinic unsaturation with a phosphorus trihalide in the presence of a Friedel-Crafts catalyst, perferably consisting of an aluminium halide, to form a reaction product having halogen atoms attached to phosphorus, and thereafter reacting the reaction product with a hydroxy compound, preferably water or methanol, to remove one or both of the halogen atoms attached to the phosphorus atom. Such intermediates will hereinafter in this specification and the claims appended hereto be referred to as "an intermediate of the type described".

According to the present invention there is provided a heterocyclic phosphorous mono-, di- or polyester having the constitution of the product prepared by reacting an intermediate of the type described with a di- or polyol or derivative thereof capable of yielding the di- or polyol on hydrolysis.

It is preferred to react the di- or polyol or derivative thereof with the intermediate of the type described wherein both halogen atoms have been replaced.

Preferred di- or polyols for use in the present invention are compounds having the following general formula:-

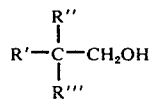

wherein R' is a hydrogen atom, an alkyl group, preferably a methyl or ethyl group, an alkylol group, preferably a methylol group, the group $-O(R''''-O)_v H$ or the group

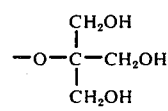

R'' and R''' are the same or different and each is a hydrogen atom, an alkyl group, preferably a methyl or ethyl group, or an alkylol group, preferably a methylol group; R'''' is an alkylene group, preferably an ethylene or propylene group; $v$ is zero or an integer, preferably an integer of from 1 to 10; and the combination of R', R'' and R''' is such that the compound contains at least two hydroxyl groups. Derivatives of such di- or polyols which may usefully be employed include the monoethers, oxides, oxetanes and carbonates thereof.

Examples of suitable di- or polyols which may be used include glycols, such as ethylene, propylene, butylene or neopentyl glycols or the oxides thereof, polyoxyethylene and polyoxypropylene glycols.

It is particularly preferred, however, to use a polyol of the formula:-

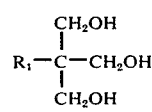

wherein $R_1$ is an alkyl group, preferably a methyl or ethyl group or an alkylol group, preferably methylol, or the group

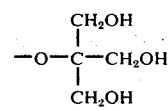

notable examples of such polyols being trimethylol propane and pentaerythritol.

It is particularly preferred to use oxetanes or carbonates derived from the aforementioned polyols.

In a further aspect of the invention the reaction product of the intermediate of the type described and a di- or polyol or derivative thereof may be further reacted with a dicarboxylic acid or derivative thereof, for example, an anhydride a lower alkyl ester thereof which is capable of reacting to form the required ester.

Examples of suitable dicarboxylic acids include sebacic, azelaic, adipic, glutaric, maleic and succinic acids and alkyl and alkenyl succinic acids, e.g. dodecenyl and polybutenyl succinic acids. Alternatively the so-called "Dimer acids," obtainable by the dimerisation of unsaturated fatty acids such as linoleic acid, may be employed. In general these acids may be described as having the formula:-

$$HOOC - R - COOH$$

wherein R is an alkylene, hydrocarbon substituted alkylene, arylene, alkarylene or aralkylene radical. Preferably R is a saturated or unsaturated, straight or branched chain alkylene radical containing from 2 to 200 carbon atoms, possibly including in its structure a saturated or unsaturated ring.

The mono-, di- or polyesters which are the subject of this invention are difficult to characterise and will invariably consist of mixtures of products having the general empirical formula:-

$$A_m B_n D_p$$

wherein each A is the same or different and is believed to have the structure,

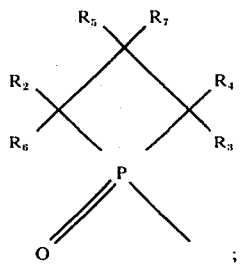

each B is the same or different and has the formula $(-O)_y-R_8-(OH)_x$;

each D is the same or different and has the formula $-OC-R-CO-$;

$m$ and $n$ are integers of from 1 to 20; and
$p$ is zero or an integer of from 1 to 20.
In each group B:-
  $x$ is zero or an integer of from 1 to 7;
  $y$ is an integer of from 1 to 8; and
  $(x+y)$ is an integer of from 2 to 8.
For the molecule as a whole:-
  $n\,x$ is preferably at least 1, more preferably at least 2; and
  $2p+m=ny$.

The groups A, B and D may be linked together in one of the following ways:-

AB, ABA, ABDB, ABDBA, ABDBDBA,

ABDBDBA, ABA etc. etc.
   |     |
  A     D
        |
        B wherein it is understood that the values of $x$ and $y$ are chosen such that there are no free valencies and wherein R is as defined above; $R_2$ and $R_3$ are the same or different and are straight or branched chain hydrocarbon groups, at least one containing at least 20 and preferably at least 30 carbon atoms, $R_3$ more preferably being hydrogen, methyl or ethyl and $R_2$ more preferably containing at least 40 carbon atoms; $R_4$, $R_6$ and $R_7$ are the same or different and may be hydrogen or hydrocarbon, preferably hydrogen, methyl or ethyl; $R_5$ is hydrogen or methyl; and $R_8$ is an alkylene, oxyalkylene or polyoxyalkylene group. The groups $R_2$, $R_3$, $R_4$, $R_5$, $R_6$ and $R_7$ are usually derived from polypropylene or polyisobutylene having a molecular weight of from 700 to 3500 and therefore usually contain collectively from 50 to 250 carbon atoms.

B is preferably derived from trimethylol propane or pentaerythritol.

The invention also includes a process for the preparation of heterocyclic phosphorus mono-, di- or polyesters suitable as lubricating oil additives which process comprises reacting a compound of the formula:-

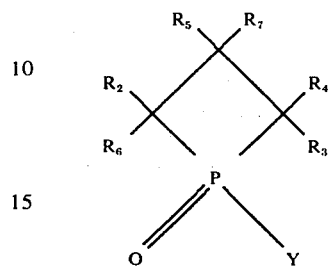

wherein $R_2$, $R_3$, $R_4$, $R_5$, $R_6$ and $R_7$ are as hereinbefore defined and Y is a halogen atom or a hydroxyl group, preferably a hydroxyl group, with a di- or polyol or derivative thereof as hereinbefore defined, and optionally, thereafter reacting the product with a dicarboxylic acid or derivative thereof and further di- or polyol if desired, to form mono-, di- or polyesters of the type hereinbefore described.

It is preferred to use a derivative such as the oxetane or carbonate of a polyol or the oxide of a diol in carrying out the initial esterification.

The intermediate of the type described, believed to be a phosphinic acid or phosphinic acid halide of the above proposed general formula, and the di- or polyol or derivative thereof may be reacted together at the highest temperature possible depending on the boiling point of the reactants but not so high as to degrade the hydrocarbon chain. Thus, temperatures much in excess of 260°C should be avoided and the reaction is usually carried out at a temperature between 180° and 200°C. However, when the lower alkylene oxides are used at atmospheric pressure, the temperature of the reaction will be ambient temperature or slightly below, i.e. from about 10°C upward.

The reactants are heated together for sufficient time and at a sufficiently high temperature to give a reasonably low acidity, preferably less than 5 mg KOH/g and it is desirable that the acidity should be less than 3mg KOH/g.

The esterification of these products with dicarboxylic acids is carried out under normal esterifcation conditions using small amounts of known esterification catalysts in a water carrying solvent such as benzene, toluene or xylene, the latter being preferred.

The acidity of these esters again should be as low as possible, preferably less than 10mg KOH/gm and more desirably less than 5mg KOH/g.

It is to be understood that in another aspect the invention provides a lubricating composition comprising a major amount of lubricating oil and a minor amount, e.g. from 0.1 to 10% by weight, based on the total weight of the lubricating composition, of a mono-, di- or polyester as hereinbefore described.

There now follows by way of example typical preparations and compositions in accordance with the present invention, wherein amounts and proportions of phosphinic acid and phosphinic acid halide intermediates expressed as "equivalents" are equivalents based on phosphorus content.

EXAMPLE 1

To 133.2g (1 mole) of anhydrous aluminium trichloride, dissolved in 100 ml methylene dichloride in a glass vessel cooled in an acetone/dry ice bath, were added over 10 mins. 137.6g (1 mole) of phosphorus trichloride in 100 ml methylene dichloride. To this was added 840g (1 mole) of polypropylene having a molecular weight of 840 dissolved in 500 ml of methlene dichloride over 35 minutes whilst maintaining the temperature below 8°C and with continuous stirring. The reaction mixture was stirred for a further 3 hours at from 5° to 10°C, a further 250 ml of methylene dichloride being added after 2 hours. 500 ml methanol were then added whilst maintaining the temperature below 15°C. The temperature of the mixture was then allowed to rise to room temperature over one-half hour with continued stirring. The resultant solution was filtered through "Speed flow" filter-aid and the pad was then washed with methylene dichloride and commercial hexane of boiling range 62° – 68°C (designated S.B.P. 62–68). The lower, methanol, layer of the filtrate was discarded and the upper layer washed with 500 ml of methanol/water (1:1 by volume). The lower layer now contained the product and this was stripped and steam hydrolysed for 12 hours on an oil bath at 160°C. The product was dissolved in S.B.P. 62–68, washed four times with 250 ml aliquot portions of methanol/$H_2O$ (1:1 by volume) and stripped to a bath temperature of 175°C/6mm. The product was filtered hot through "Speed plus" filter-aid to yield 661g (73%) of a polypropylene phosphinic acid containing 2.45% P (calc 3.43%). This would amount to a 65% conversion of the polypropylene. This was confirmed by acidity and saponification value determination and by column chromatography using activated alumina.

138g (0.1 equivalents) of this product (designated Intermediate I hereinbelow) was placed in a 3 necked glass flask fitted with stirrer, nitrogen bleed and dropping funnel. 12.8g (0.11m) of trimethylol propane oxetane (3 - ethyl - 3 hydroxymethyl oxetane) was added at room temperature with stirring and the bath temperature raised to 180°–190°C for 6 hours until the acidity of the product was reduced to 1.1mg KOH/g, the acidity of the starting material being 34.8mg KOH/g. The product was stripped under vacuum (2mm) to a bath temperature of 210°C, then filtered at 100°C through Speed plus. 125g of product (83%) were obtained, containing 1.96% phosphorus (calc 2.06%). Similar batches were prepared containing varying amounts of phosphorus and these were used in certain of the later Examples, being designated "compound A" in each case.

The trimethylol propane oxetane employed in this Example was prepared from trimethylol propane (3.0 moles), diethyl carbonate (3.0 moles) and 1 pellet of NaOH by reaction at a bath temperature of 150°C and thereafter removing excess diethyl carbonate (274g) by distillation and removing ethanol up to a still-head temperature of 80°C. The residue was heated at a bath temperature of 240°C under 40–50 mms Hg vacuum, yielding 296g (85%) mobile distillate as desired product.

EXAMPLE 2

A similar preparation was carried out using a large excess of trimethylol propane instead of the oxetane used in the previous example. In this manner the acidity of the product was reduced to 3.3mg KOH/g after 45 hours. The acidity was further reduced to 1.4mg KOH/g after a further 7 hours reaction with a small quantity of trimethylolpropane oxetane.

EXAMPLE 3

A similar preparation to that of Example 1 was carried out using 31.8g (0.024 equivalents) of the same intermediate phosphinic acid and 4.05g (0.025 mole) of pentaerythritol carbonate, an additional 2g of the carbonate being added during the course of the reaction. The acidity was reduced to 1.7mg KOH/g after 26 hours. The product was taken up in S.B.P. 62/68 and filtered, 1.6g of pentaerythritol being recovered. The solvent was removed by stripping to a temperature of 185°C under a pressure of 4mmHg. The product was filtered hot, 13.8g (43.5%) being obtained and was found to contain 2.18% P (Calc 2.13%). The pentaerythritol carbonate was prepared by transesterification of 68g (0.5 mole) of pentaerythritol with 59g (0.5 mold) diethyl carbonate in 100 ml of dimethyl formamide in the presence of a small amount of sodium hydroxide (0.5g approx.). 49.7g (calculated 46g) of ethanol were distilled off through a packed column during the reaction.

EXAMPLE 4

15g of an ester product similar to that obtained in Example 1 and 1g of maleic anhydride were refluxed in 10 ml xylene for 3 hours. A further 15g of the ester in 20 ml of xylene were then added and the xylene removed by distillation at atmospheric pressure. The material was then stripped under a vacuum of 280 mm at 190°C bath temperature and filtered to yield 18.8g of a product containing 1.91%P (calc 2.02%).

In certain cases other intermediates were used. These intermediates were prepared in substantially the same manner as that of Example 1 which is designated Intermediate I.

Intermediate II

Several preparations were carried out to form an acid chloride. The preparation was substantially the same as in Example 1 except for the work up procedure in which 500mls of anhydrous methanol and 2 × 50mls aqueous methanol per mole of a commerically available polyisobutylene (PIB) having a molecular weight of 1000 were used. The batches were combined and the product steam hydrolysed for several hours, extracted with special boiling spirit 62/68, washed with 1:1 water/methanol and stripped under vacuum to about 180°C. The product contained 1.63%P and 0.25%Cl.

Intermediate III

This was derived from a commercially available polyisobutylene (PIB) of molecular weight 1300 (1950g, 1.5 moles). $PCl_3$(205g 1.5 moles), $AlCl_3$(240g, 1.88 moles). These were reacted for one hour at a temperature of 5° to 10°C in 1500ml of dichloromethane. 800ml of dry methanol were added and a white precipitate filtered off and the methanol layer was discarded. The dichloromethane layer was washed twice with 500 ml of 1:1 $H_2O$/methanol, dried, filtered and steam hydrolysed for 14 hours.

The product was extracted with special boiling spirit, boiling point 62/68, washed with 500 mls 1:1 $H_2O$/methanol and stripped to 180°C/5mm Hg. 1390g (68%) of product was obtained and found to contain 1.0%P and 0.32%Cl.

The preparation of further compounds was carried out using a process substantially the same as in Examples 1 to 3, the amounts of staring materials and analysis of products being given in Table I wherein the respective preparations are designated Examples 5 to 8.

(PTSA) were then added and refluxed for a further 31 hours; two portions each of 0.3g (total 20% excess) of trimethylol propane were added after 12 and 28 hours. The product was filtered, washed with 50ml 1:1 aqueous methanol, separated, dried and stripped. The yield

TABLE I

| | Example 5 | Example 6 | Example 7 | Example 8 |
|---|---|---|---|---|
| Intermediate | I(ex.840mw Polypropylene) | I(ex. 840mw Polypropylene) | II(ex.1000mw PIB) | III(ex.1300mw PIB) |
| Equivalents (based on P) | 0.05 | 0.1 | 0.075 | 0.4 |
| Di- or polyol or derivative | Trimethylol propane carbonate | Ethylene Oxide | Trimethylol propane oxetane | Trimethylol propane oxetane |
| weight (g) | 8.28 | | 9.56 | 46.5 |
| | | 200ml. | | |
| moles | 0.08 | | 0.0825 | 0.4 |
| solvent | | 100ml. SBP 62/68 | | |
| Temperature of Reaction °C | 220–260 | 15–75 | 190–200 | 190–200 |
| Time of Reaction (hours) | 28 | 14 | 17 | 20 |
| Comments | Small amounts of trimethylol propane oxetane added during reaction to reduce acidity. | The ethylene oxide was cooled to 0°C and blown into the reaction mixture with dry $N_2$. Solvent and used epoxide was recycled after being caught in a cold trap. | | 3 portions of 2g. of oxetane added during reaction. |
| Found %P | 2.19 | 2.1 | 1.57 | 1.2 |
| Calc. | 2.04 | 2.08 | 1.54 | 0.97 |
| Acidity mg. KOH/g. | 4.9 | 3.7 | 1.5 | 4.2 |
| Yield Wt.(g) | 51 | 102 | 138 | 1000 |
| % | 69 | 69 | 92 | 80 |

EXAMPLE 9

87.5g (0.06 equivalents) of a product similar to that of Example 1 (hereinafter designated compound A) and 17g (0.03m) Empol dimer acid were heated under nitrogen for 6 hours at 195°C, after which time the residual acidity was 6.6mg KOH/g. Further reaction for a total of 32 hours at temperatures up to 225°C failed to lower the acidity, despite the addition of 5% and 10% excess of the product similar to that of Example 1 at 17 and 26 hours. The product was filtered hot through Speed-plus, whereupon 93g (87%) was obtained which was found to contain 1.89%P (calc. 1.8).

EXAMPLE 10

This product was prepared in substantially the same manner as in Example 9, except that 98g (0.066 equivalents) of A and 17.5g (0.033m) of a polyisobutenyl succinic anhydride derived from a PIB of mw 425, were used in the reaction. The total reaction time was 35 hours. 5% and 10% of A was added at 12 and 23 hours. 75g (83.5%) of a product was obtained having an acidity of 16.9mg KOH/g and containing 1.99%P (calc. 1.82).

EXAMPLE 11

75.1g (0.05 equivalents) of A and 4.9g (0.5m) of maleic anhydride were refluxed in 60ml of xylene until the anhydride content (infrared analysis), residual acidity or water yield indicated sufficient reaction, which took about 3 hours. 4.0g (0.03 moles) trimethylol propane and 0.2g of paratoluene sulphonic acid was 85% and the acidity 7.0mg KOH/g and the product was found to contain 1.94%P (calc. 1.88).

EXAMPLE 12

The reaction was carried out substantially the same as in Example 11 with the following parameters: 58.3g (0.04 equivalents) of A, 4g (0.04m) succinic anhydride, 50ml xylene, 2.68g (0.02 mole) trimethylol propane and 0.2g PTSA added after 2½ and refluxed for a total of 20 hours, additional PTSA and solvent being added after 6 hours. Yield = 65%, %P = 1.86 (Calc. 1.93), acidity = 2.0mg KOH/g.

EXAMPLE 13

Substantially as in Example 11, with the following parameters: 75.1g (0.05 equivalents) of A, 7.3g (0.05 moles) adipic acid, 5.0ml xylene. 3.35g (0.025 moles) trimethylol propane and 0.2g PTSA added after 1½ hours. Total reflux time 30½ hours. Additional PTSA and solvent added after 5¾, 11¾ and 18 hours. Yield 75%, %P = 1.95 (Calc. 1.81). Acidity = 3.8mg KOH/g.

EXAMPLE 14

The reaction was carried out substantially as in Example 11, with the rollowing parameters: 60.5g (0.04 equivalents) of A and 40 g (0.04 moles) Empol 1014 dimer acid were refluxed for 1½ hours and 2.68g (0.02 moles) of trimethylol propane were added, the reaction being continued for a total of 25½ hours. Additional solvent and PTSA were added after 6¾, 12¾ and 19 hours. Yield = 81%, %P = 1.56 (Calc. 1.45). Acidity = 2.0mg KOH/g.

EXAMPLE 15

The reaction was carried out substantially as in Example 11, with the following parameters: 1158g (0.36 equivalents) product of Example 8, 52.6g (0.36 moles) adipic acid and 1.2g PTSA were refluxed for 2½ hours. 24.2g (0.18 moles) of trimethylol propane were added and refluxed for a further 9 hours. Yield = 78%, %P = 1.09% (Calc. 0.91). Acidity = 3.8mg KOH/g.

EXAMPLE 16

The reaction was carried out in substantially the same manner as in Example 11, with the following parameters: 144.6g (0.1 equivalents) of A, 14.6g (0.1 moles) adipic acid and 0.15g PTSA were refluxed in xylene for 2 hours. 13.6g (0.1 moles) pentaerythritol were added and refluxing continued for 3 hours. The solvent was removed and the mixture heated at 180°C for a further 4 hours. 1.36g pentaerythritol were added and heating continued at 180°–200°C for 4 hours. Yield = 68%, %P = 1.91% (Calc. 1.83). Acidity = 4.1mg KOH/g.

EXAMPLE 17

144.8g (0.1 equivalents) of a product prepared in a similar manner to that of Example 3, 14.6g (0.1 moles) adipic acid and 0.3g PTSA were refluxed in xylene for 3½ hours. 6.8g (0.05m) pentaerythritol were added and the mixture refluxed for 3 hours. The solvent was removed and the mixture heated at 190°–200°C for 6 hours. 2g pentaerythritol was added and the heating continued for a further 6 hours. Yield = 79%, %P = 2.02% (Calc. 1.90). Acidity = 8.7mg KOH/g.

EXAMPLE 18

66.5g (0.05 equivalents) of Intermediate I were reacted by stirring at 200°–220°C for 18 hours with a total of - moles (21.25g) of tris methyl diglycol orthoformate, previously prepared by transesterification of methyl diglycol with triethyl orthoformate. Stripping of the product yielded a residue of 58g (81% yield), %P = 2.24 (Calc. 2.16). Acidity = 5.8mg KOH/g.

EXAMPLE 19

66.5g (0.05 equivalents) of Intermediate I were reacted at 200°–240°C for 29½ hours with 2 portions of 15.4g (0.055 moles) of "dipentaerythritol carbonate" [previously prepared by transesterification of dipentaerythritol (0.25 moles) with diethyl carbonate (0.25 moles) in dimethyl formamide solution and catalysed by one pellet of NaOH, with the removal of 16.4g of ethanol]. The acidity dropped to 13mg KOH/g and was lowered to 7mg KOH/g by reaction at 200°–240°C with 3g of trimethylol propane oxetane. The product was filtered in S.B.P. 62/68 solution, stripped and filtered at 100°C through a filter aid. Yield = 51g (65%), %P = 2.17 (Calc. 1.98). Acidity = 11.0mg KOH/g.

The effectiveness of the above products was demonstrated by dissolving 3.5% by weight of the above-mentioned compounds in place of the dispersant in a fully formulated MIL - L -2104C formulation and testing the formulation so prepared in the well known "Panel Coker Test". The results of these tests are given in Table II.

The tests were carried out in a slightly modified form of the normal apparatus. Instead of continuous oil splashing, the oil was splashed against the aluminium panel maintained at 600°F for 3½ hours using a timing device to give a 15 second splash and 45 second period when the paddle was stationary. The apparatus was further modified to allow a flow of moist air through

TABLE II

| Example No | Dispersant | | Sump % Merit Rating | Panel Rating | Panel Wt. Gain(mg) |
|---|---|---|---|---|---|
| 20 | Product of Example | 1. | 94.6 | 1–0 | 10 |
| 21 | (4 different batches) | | 88.0 | 3–0* | 28 |
| 22 | | | 87.5 | 3–0 | 14 |
| 23 | | | 88.5 | 3–0 | 9 |
| 24 | Product of Example | 2. | 85 | 3–0 | 15 |
| 25 | " | 3. | 78.5 | 4–0 | 17 |
| 26 | " | 5. | 92.2 | 4–0 | 19 |
| 27 | " | 6. | 74.8 | 3–0 | 12 |
| 28 | " | 7. | 88.5 | 3–0* | 12 |
| 29 | " | 8. | 90.2 | 3–0 | 20 |
| 30 | " | 9. | 88.0 | 3–0 | 13 |
| 31 | " | 10. | 89.3 | 3–0* | 20 |
| 32 | " | 11. | 83.7 | 3–0* | 15 |
| 33 | " | 12. | 88.0 | 3–0 | 18 |
| 34 | " | 13. | 88.0 | 3–0* | 22 |
| 35 | " | 14. | 83.3 | 3–0 | 23 |
| 36 | " | 15. | 87.3 | 2–0 | 5 |
| 37 | " | 16. | 90.2 | 3–0 | 14 |
| 38 | " | 17. | 87.5 | 3–0 | 14 |
| 39 | " | 18. | 94.9 | 3–0* | 15 |
| 40 | " | 19. | 93.1 | 3–0 | 17 |
| Commercially available Mannich base+derived from 1900mw PIB used in 5.4% concentration. | | | 74.5 60.5 | 3–0 3–0 | 29 12 |
| Commercially available ester of a polyisobutenyl succinic acid derived from 1000mw PIB and pentaerythritol. | | | 68 78 | 3–0 3–0 | 35 18 |

+PIB substituted phenol/formaldehyde/polyamine condensation product.
*Indicates a band of lacquer.

the sump above the oil surface at the rate of 2.3 liters per hour.

The weight change and appearance of the panels were observed after test, the appearance of the panels being assigned merit ratings which were determined by comparing with a set of 28 panels divided into four groups. Where the panels were merely stained these panels were given numbers 1 – 7 in increasing order of staining, i.e. number 1 was practically clean and number 7 was black, the number being followed by the suffix "O" indicating "ordinary" staining. In the second group the same numbers were assigned 1 – 7 but the suffix "L" was placed after the number to indicate that it had the same staining but was lacquered. Similarly in group 3 the suffix "B" showed the appearance of bubbles on the same background. In group 4, the suffix "S" showed that the panel was sooted, the number referring to the panel colour. A rating of 4 – 0 or less was considered to be reasonable.

In addition to the foregoing rating of the panels, the area of the sump not normally immersed in oil was rated according to the percentage cleanliness in much the same manner as an engine piston is rated after a test such as the Caterpillar 1-G test. It is believed that the above-mentioned test correlates well with the Caterpillar 1-G Engine Test.

It will be noticed that in general the products of the present invention give a significantly improved sump rating over the prior art products.

We claim:

1. A heterocyclic phosphorus mono- or polyester product prepared by reacting a polyol of the formula:

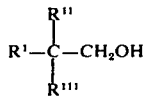

wherein R' is selected from the group consisting of hydrogen, methyl, ethyl, methylol, the group -O(R''''-O)$_v$H where R'''' is ethylene or propylene and $v$ is zero or an integer of from 1 to 10, and

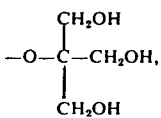

R'' and R''' are the same or different and each is selected from the group consisting of hydrogen, methyl, ethyl and methylol, and the combination of R', R'' and R''' is such that at least two hydroxyl groups are present; or a monoether, oxide, oxetane or carbonate which yields said polyol on hydrolysis; with a heterocyclic phosphorus compound prepared by reacting an olefin polymer or copolymer having a molecular weight in the range of about 700 to 3500 and containing olefinic unsaturation with a phosphorus trihalide in the presence of a Friedel-Crafts catalyst to form a reaction product having hydrocarbon and halogen attached to phosphorus, and thereafter reacting the reaction product with water or methanol to remove one or both of the halogen atoms from the phosphorus atom; and further reacting the reaction product of said polyol and heterocyclic phosphorus compound with a hydrocarbon dicarboxylic acid, or an anhydride or ester thereof.

2. A product according to claim 1 wherein the dicarboxylic acid is selected from the group consisting of sebacic, azelaic, adipic, glutaric, maleic, succinic, alkyl succinic and alkenyl succinic acids.

3. A product according to claim 1 wherein the dicarboxylic acid has the general formula:-

wherein R is selected from the group consisting of alkylene, hydrocarbon substituted alkylene, arylene, alkarylene and aralkylene radicals.

4. A product of claim 1 wherein said olefin polymer is polyisobutylene or polypropylene.

5. A product of claim 1 wherein said polyol is trimethylolpropane or pentaerythritol.

6. A product of claim 1 wherein said hydrocarbon dicarboxylic acid is an alkyl or alkenyl succinic acid or anhydride.

7. A process for the preparation of a heterocyclic phosphorus mono- or polyester product comprising reacting a polyol of the formula:

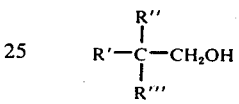

wherein R' is selected from the group consisting of hydrogen, methyl, ethyl, methylol, the group -O(R''''-O)$_v$H where R'''' is ethylene or propylene and $v$ is a zero or an integer of from 1 to 10, and

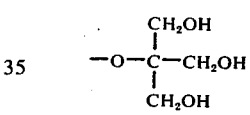

R'' and R''' are the same or different and each is selected from the group consisting of hydrogen, methyl, ethyl and methylol, and the combination of R', R'' and R''' is such that at least two hydroxyl groups are present; or a monoether, oxide, oxetane or carbonate which yields said polyol or hydrolysis; with a heterocyclic phosphorus compound prepared by reacting an olefin polymer or copolymer having a molecular weight in the range of about 700 to 3500 and containing olefinic unsaturation with a phosphorus trihalide in the presence of a Friedel-Crafts catalyst to form a reaction product having hydrocarbon and halogen attached to phosphorus, and thereafter reacting the reaction product with water or methanol to remove one or both of the halogen atoms from the phosphorus atom; and further reacting the reaction product of said polyol and heterocyclic phosphorus compound with a hydrocarbon dicarboxylic acid, or an anhydride or ester thereof.

8. A process according to claim 7 wherein the product of the reaction with the dicarboxylic acid or derivative thereof is reacted with further di- or polyol or derivative thereof.

9. A process according to claim 7 wherein said olefin is polyisobutylene or polypropylene.

10. A process according to claim 7 wherein said polyol is trimethylolpropane or pentaerythritol.

11. A process according to claim 7 wherein said hydrocarbon dicarboxylic acid is an alkyl or alkenyl succinic acid or anhydride.

* * * * *